US005891093A

United States Patent [19]

Dysarz

[11] Patent Number: 5,891,093

[45] Date of Patent: Apr. 6, 1999

[54] TRAP IN HUB CHAMBER SAFETY NEEDLE CANNULA SYRINGE TIP

[76] Inventor: Edward D. Dysarz, 11423 Triola La., Houston, Tex. 77072

[21] Appl. No.: 987,452

[22] Filed: Dec. 9, 1997

[51] Int. Cl.$^{6}$ .................................................... A61M 5/00

[52] U.S. Cl. ......................... 604/110; 604/192; 604/240; 604/272

[58] Field of Search .................................... 604/272, 101, 604/107, 192, 197, 199, 239, 240, 273, 263, 110

[56] References Cited

U.S. PATENT DOCUMENTS 3,008,570 6/1961 Roehr et al. .
3,107,785 10/1963 Roehr .
3,306,291 2/1967 Burke .
3,895,633 7/1975 Bartner et al. .
4,300,678 11/1981 Gyure .
4,356,822 11/1982 Hall .
4,425,120 1/1984 Sampson .
4,639,249 1/1987 Larson .
4,655,751 4/1987 Harbaugh .
4,816,022 3/1989 Poncy .
4,840,619 6/1989 Hughes .
5,084,019 1/1992 Gartz ...................................... 604/110
5,084,020 1/1992 Gartz ...................................... 614/110

*Primary Examiner*—Wynn Wood Coggins
*Assistant Examiner*—N. Kent Gring

[57] ABSTRACT

A syringe tip device and method wherein a safety chamber is provided at the end of the hub for a slip tip, eccentric tip, or threaded tip syringe. The hub is placed on any conventional syringe in a convention manner; the safety sheath protecting the needle cannula is removed and the syringe is filled with the desired amount of medication wherein the medication is injected into a patient wherein when the process is complete, a button or lever is depressed, releasing an internal biased spring that strikes the needle cannula and bends the needle cannula within the hub chamber until the entire needle cannula is bent and destroyed within the hub chamber thus rendering the needle cannula safe from an accidental needle cannula prick.

10 Claims, 4 Drawing Sheets

8
4
6
14
7
17
18
16
13
1
2

9
23
14
18
19
24
4
9
13

TRAP IN HUB CHAMBER SAFETY NEEDLE CANNULA SYRINGE TIP

BACKGROUND OF THE INVENTION

There are many safety syringe designs available today. Some of these designs have a sleeve or a sheath that will cover the needle after it has been used. Some typical designs with sleeves or sheaths are Z. M. ROEHR et al U.S. Pat. No. 3,008,570, Z. M. ROEHR U.S. Pat. No. 3,107,785, BARTNER, et al U.S. Pat. No. 3,895,633, G. K. BURKE U.S. Pat. No. 3,306,291, GYURE et al U.S. Pat. No. 4,300,678, WINSTEAD HALL U.S. Pat No. 4,356,822, SAMPSON U.S. Pat. No. 4,425,120, LARSON U.S. Pat. No. 4,639,249, HARBAUGH U.S. Pat. No. 4,655,751, STRAUSS U.S. Pat. No. 4,664,654 , BRAGINETZ U.S. Pat. No. 4,666,435, SPENCER U.S. Pat. No. 4,702,738, MILORAD U.S. Pat. No. 4,702,739, SPENCER U.S. Pat. No. 4,801,295, PONCY U.S. Pat. No. 4,816,022, and HUGHES U.S. Pat. No. 4,840,619.

Other designs have a retractable needle such as WELTMAN U.S. Pat. No. 3,306,290, and DENT U.S. Pat. No. 4,392,859. These designs do not have a means whereby the needle is extended from the syringe and held in place in a positive and rigid position in order to first inject the needle prior to injecting the medication. Most of these designs have one major purpose and that is to prevent the spread of infectious diseases such as aids, hepatitis or other diseases from an accidental injection with a contaminated needle, into others after the needle of the syringe was inserted into a patient with the above mentioned disease. These various designs all work well up to a degree, but they all fall short of their intended purpose during the act of covering the needle, or removing the needle.

All of these designs require at lease two hands to operate. The use of two hands to cover the contaminated needle is most unsatisfactory in that during the act of placing a second hand on the syringe the person holding the syringe in one hand may be bumped and accidentally inject the needle into their other hand before it can grasp the syringe. Other accidental jabbings or injections can happen in an ambulance where just as a person tries to grasp the contaminated syringe, the ambulance can hit a bump in the road causing the person holding the syringe to accidently stick another person or themselves with the contaminated needle. The need has developed for a syringe that will cover the contaminated needle with the use of only one hand.

SUMMARY

It is the object of this invention to provide a syringe wherein the needle of the syringe is retracted into the hub chamber at the end of the syringe and thereby be protected from an accidental pricking after the needle cannula has been used; the needle can be retracted into the hub chamber with the use of only one hand and that one hand being the hand that was used to inject the needle into a patient.

Another object of the present invention is to render the syringe useless after the needle is retracted into the hub chamber of the syringe and to prevent the accidental reuse of the contaminated needle cannula to further prevent the reuse and abuse by users of illicit drugs.

It is still another object of the present invention to allow for the safe disassembly of the contaminated syringe for better and safer disposal means.

The foregoing and other objects and advantages are attained by a hypodermic syringe, syringe barrel, needle cannula, spring, hub chamber assembly and plunger assembly in combination with a trigger means wherein when said syringe is used to inject a drug or other material into a patient, the trigger is released and the spring further impacts the side of the needle cannula and destroys the needle cannula in the hub chamber rendering the contaminated needle harmless to prevent the accidental pricking of others.

In accordance with still another feature of the present invention, the syringe can be safely dissembled and the needle cannula contained in the hub chamber can be safely dumped into a container for further destruction.

The features of the present invention can be best understood together with further objects and advantages by reference to the following descriptions taken in conjunction with the accompanying drawings, wherein like numerals indicate like parts.

DETAILED DESCRIPTION OF THE PREFERRED EMBODIMENT

Figure 1:
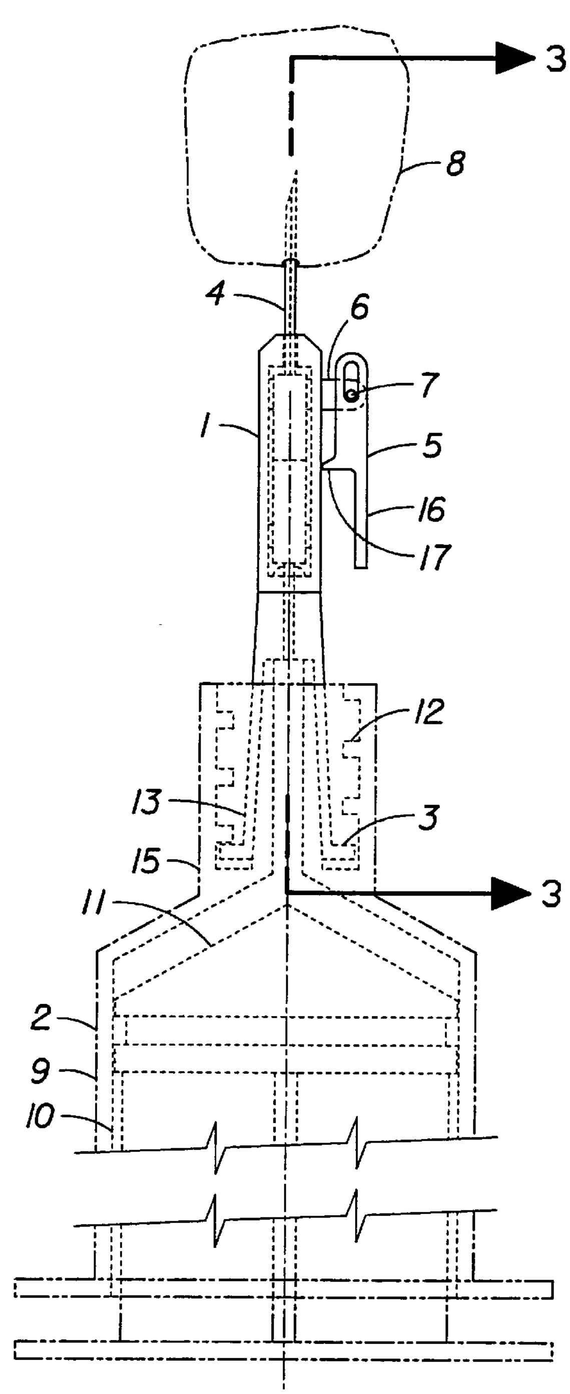
FIG. 1 is an elevation view of the device.

Referring to FIG. 1 there is shown an elevation view of the needle cannula 4, the hub chamber 14, the hub 13 suitably fixed to a syringe 2.

The first end of the needle cannula 4 is shown injected in the flesh 8 of a body; the needle cannula 4 may be inserted into a vein or artery. The second end of the needle cannula 4 extends into the hub chamber 14. The trigger means 5 is shown near the first end of the hub chamber 14. The first end of the trigger means 5 is rotateably and stably fixed to the spring stop 6 by a pivot pin 7. At the second end of the trigger means 5 is the depressor extension 16. The depressor extension shall be depressed by a finger, thumb or a corner of a table or bed. A fulcrum 17 is shown between the first end and the second end of the trigger means 5. The trigger means 5 is actuated by depressing the depressor extension 16 thereby rotating the trigger means 5 about the fulcrum 17 thereby elevating the pivot pin 7 and the spring stop 6 and thus releasing the hub spring not seen in this figure.

The hub 13 is shown at the second end of the hub chamber 14. A threaded lock 3 is shown fastened to the threaded extension 15 by the internal threads 12 formed on the inside of the threaded extension 15. Although the threaded lock (often referred to as a Luer-lock) is shown, a slip tip, eccentric tip or other type of connection could be used to fasten the hub 13 to the syringe 2.

The syringe 2 shown is any conventional mass produced syringe. The syringe 2 is shown with a barred 9, a plunger 10 and a plunger tip 11.

Figure 2:
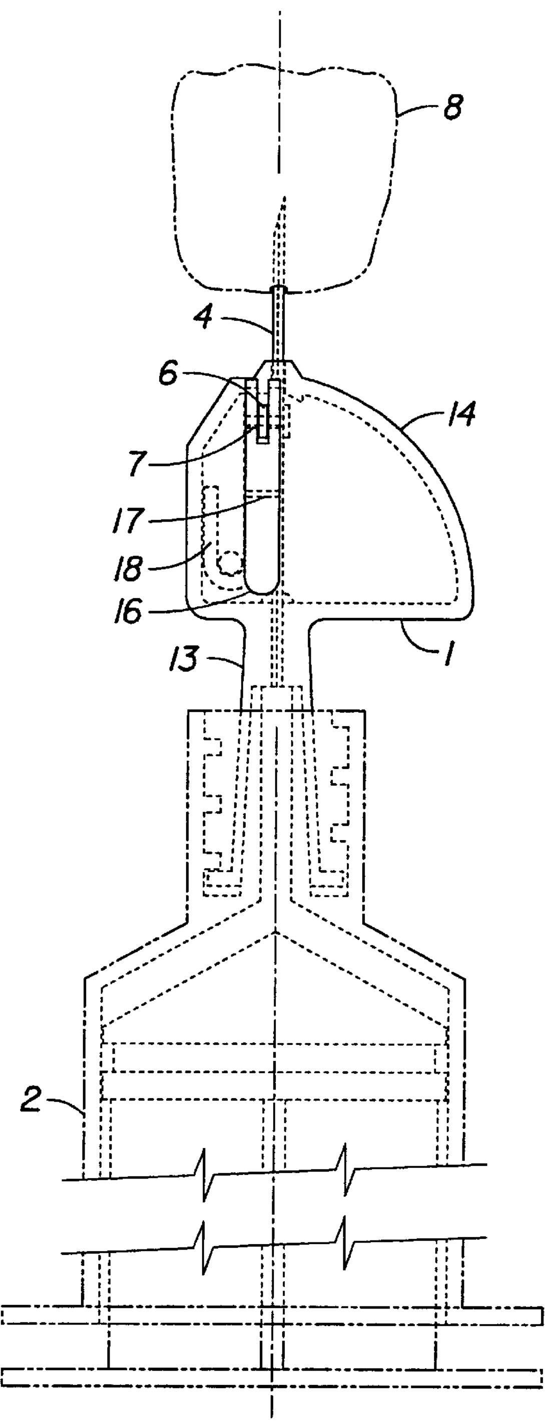
FIG. 2 is a plan view of the device.

Referring to FIG. 2 there is shown a plan view of the device 1 suitably fixed to a syringe 2.

The needle cannula 4 is shown inserted into the body 8 of a patient. The needle cannula 4 extends into the hub chamber 14 and further into the hub 13 where the hub 13 is suitably fixed to the syringe 2. The trigger means 5 is shown with the depressor extension 16 on the second end of the trigger means. The pivot pin 7 and the spring stop 6 are shown near the first end of the trigger means 5. The fulcrum 17 is shown with hidden lines below the depressor extension 16.

Figure 3:
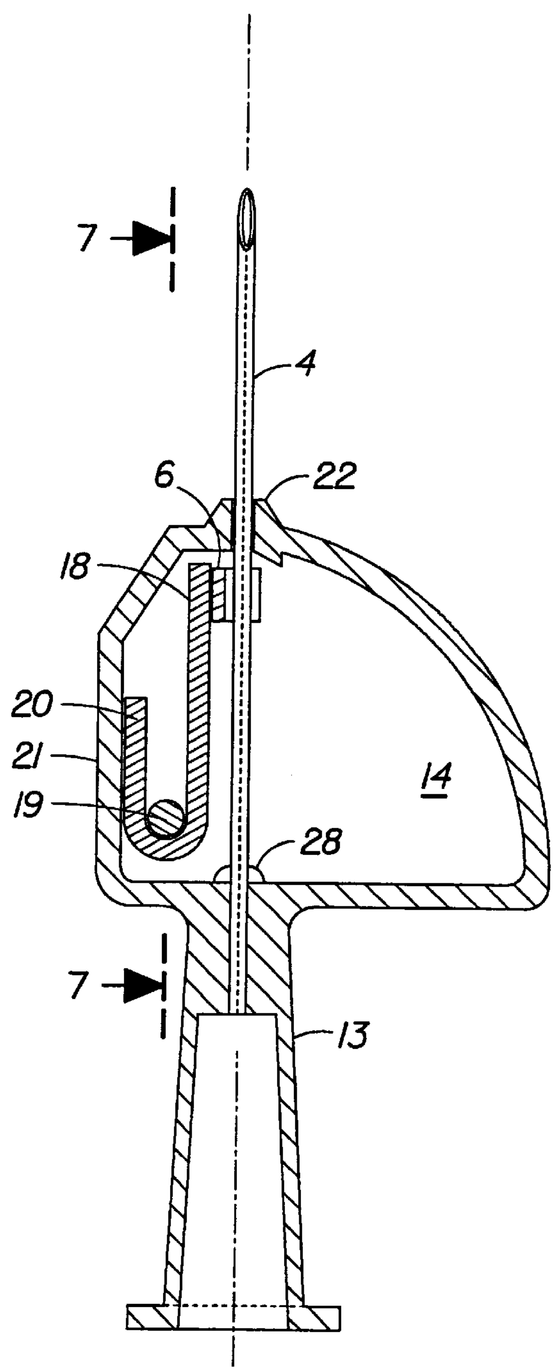
FIG. 3 is a section plan view of the device as taken through FIG. 1.

Referring to FIG. 3 there is shown a section plan view of the hub 13 and the hub chamber 14.

The hub spring 18 is shown in a biased position. The hub spring 18 is restrained by the spring stop 6 at the first end and the spring pin 19 at the second end. The hub spring lever arm 20 is part of the hub spring 18 and is restrained by the spring pin 19 and the first side 21 of the hub chamber 14.

As the needle cannula 4 extends into the hub chamber 14, the needle cannula passes through the needle cannula guide 22. The needle cannula guide 22 adds latteral stability to the needle cannula 4 as the needle cannula 4 is being injected into the flesh of a patient and the needle cannula 4 guide 22 further prevents the needle cannula 4 from moving laterally or transversably relative to the fixed position of the needle cannula 4 as the needle cannula 4 is being withdrawn from the patient or as the needle cannula 4 is being withdrawn into the hub chamber 14 while the hub spring 18 is impacting and destroying the needle cannula 4. The needle cannula 4 is also suitably fixed to the first end of the hub 13 by adhesive 28 or other suitable means.

Figure 4:
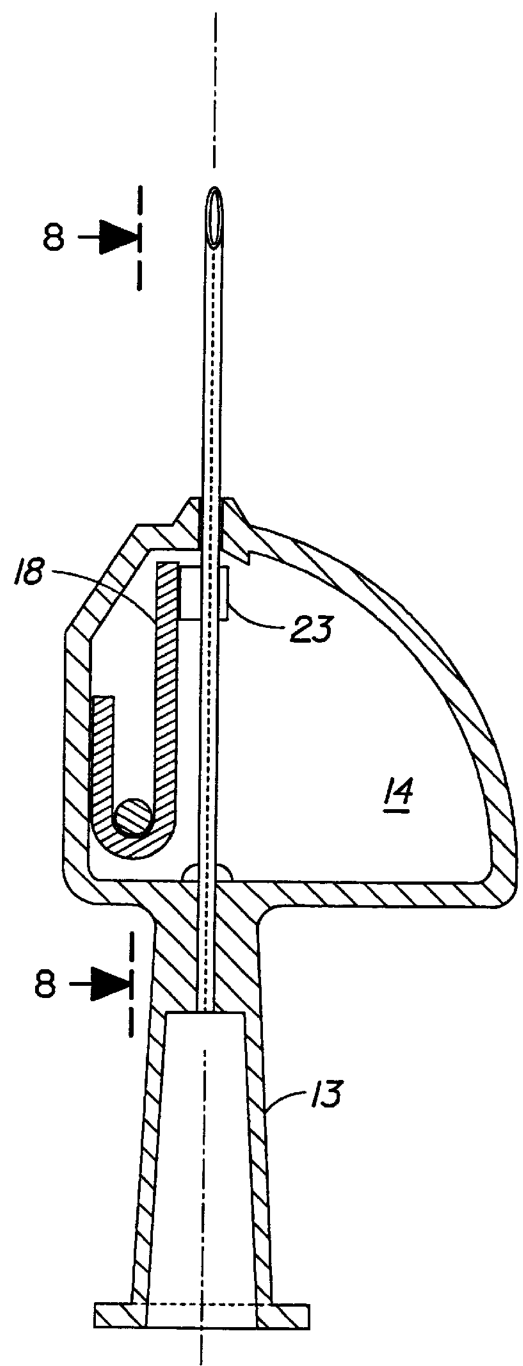
FIG. 4 is a section plan view of the device showing the spring stop removed.

Referring to FIG. 4 there is shown a section plan view of the hub 13 and the hub chamber 14.

Figure 8:
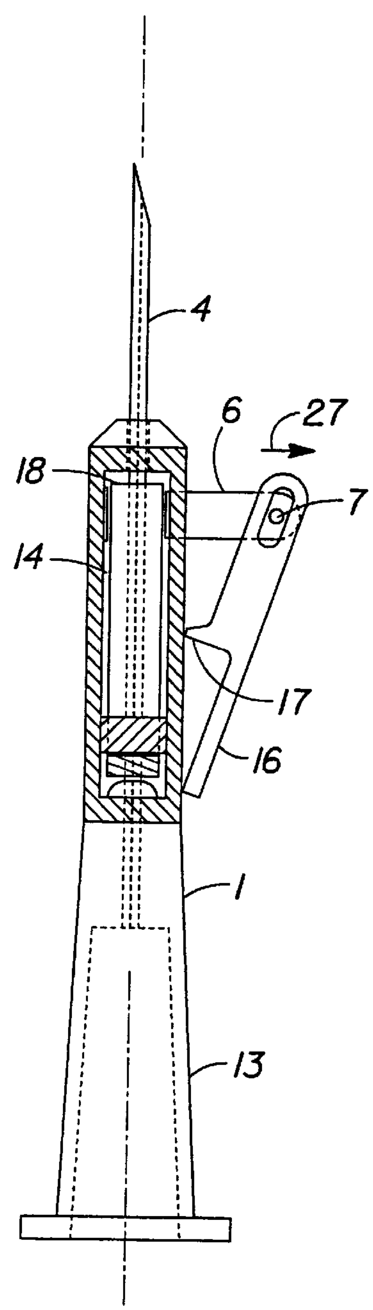
FIG. 8 is a section elevation of the device as the trigger is being actuated.

The spring stop has been withdrawn and the hub spring 18 is about to strike and destroy the needle cannula 4. This position would last for less than a tenth of a second because the hub spring 18 would snap the needle cannula 4 in an instant. The spring stop withdrawal would be as shown in FIG. 8.

The spring stop ridge 23 is seen as a raised stop on the third side near the first end of the hub chamber 14. The spring stop ridge 23 supports the second end of the spring stop while the hub spring 18 is bearing on the spring stop.

Figure 5:
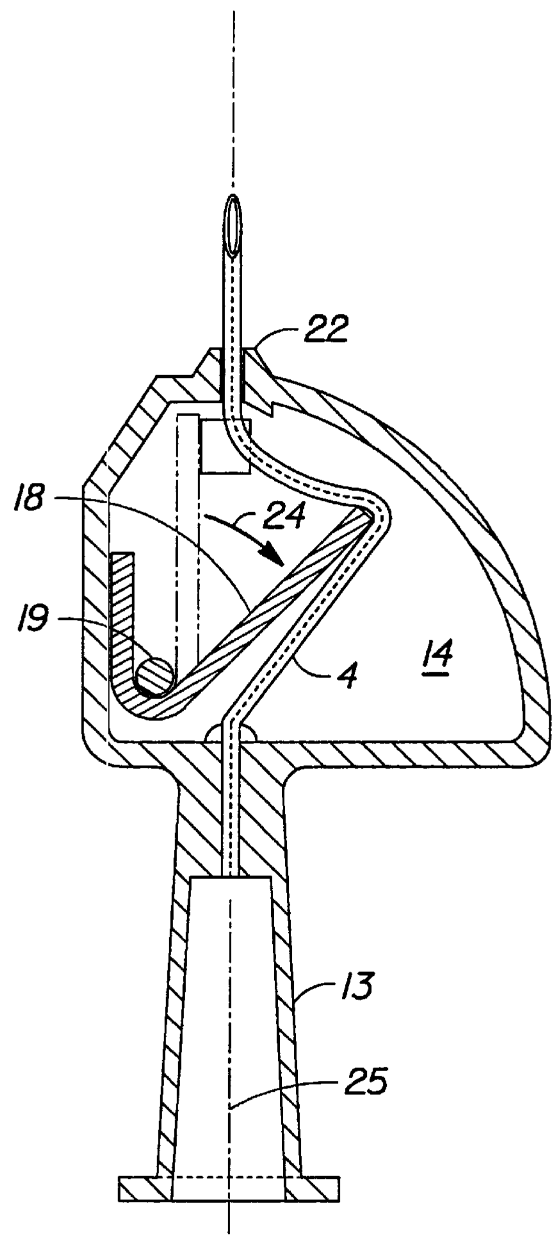
FIG. 5 is a section plan view of the device showing the spring being released.

Referring to FIG. 5 there is shown a section plan view of the hub 13 and the hub chamber 14 as the hub spring 18 starts to destroy the needle cannula 4.

The hub spring 18 has been released and is in the process of bending the needle cannula 4. The first end of the hub spring 18 is rotating 24 about the spring pin 19 while deforming the needle cannula 4. As the second end of the needle cannula 4 is being deformed on the inside of the hub chamber 14 the first end of the needle cannula 4 is being pulled directly into the hub chamber 14 without any deformation or deflection from the centerline 25 of the needle cannula 4 due to the needle cannula guide 22 that prevents the first end of the needle cannula 4 from moving in any oblique direction relative to the centerline 25, thereby forcing the needle cannula 4 to be withdrawn straight into the needle cannula guide 22.

Figure 6:
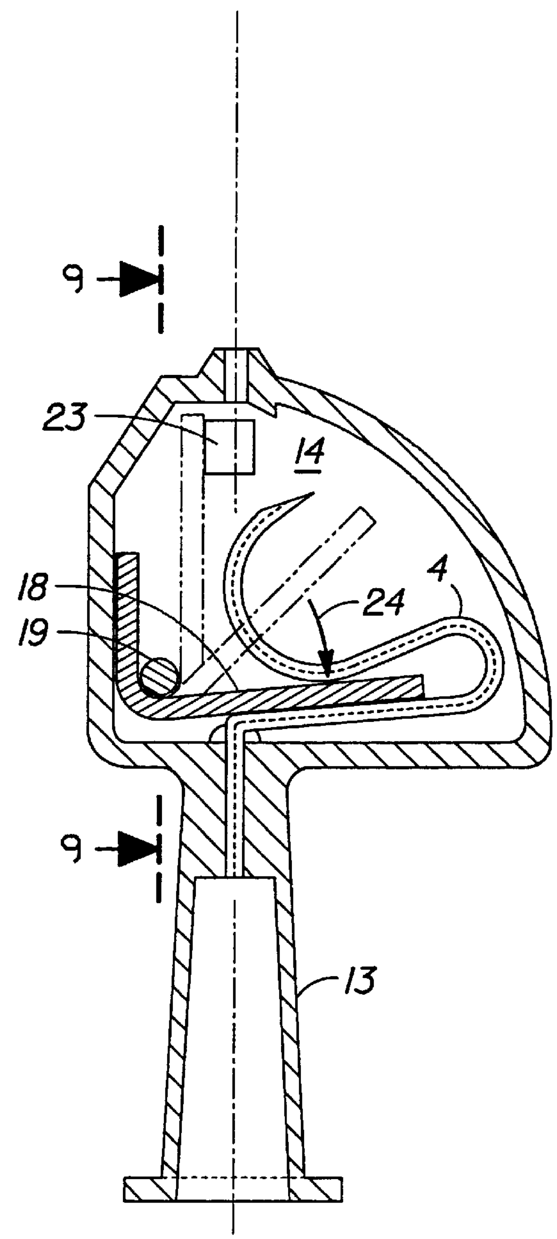
FIG. 6 is a section plan view of the device showing the needle in a destroyed position.

Referring to FIG. 6 there is shown a section plan view of the hub 13, the hub chamber 14 and needle cannula 4 destroyed.

The method of destroying the needle cannula 4 is shown. The hub spring 18 has rotated 24 about the spring pin 19 thus pulling the needle cannula 4 into the hub chamber 14 where the needle cannula 4 is bent into a useless curved needle. The movement of the hub spring 18 is sufficient to pull the entire needle cannula into the hub chamber 14 thereby rendering the needle cannula 4 useless and safe from accidental needle pricks because the entire needle cannula 4 is contained in the hub chamber 14 and it cannot come out or be reused.

The spring stop ridge 23 is also seen more clearly in this view.

The hub 13 the hub chamber 14, the needle cannula 4, the hub spring 18 and all other components contained in or on the hub 13 and the hub chamber 14 may be safely and suitably thrown away without any fear of an accidental needle prick.

Figure 7:
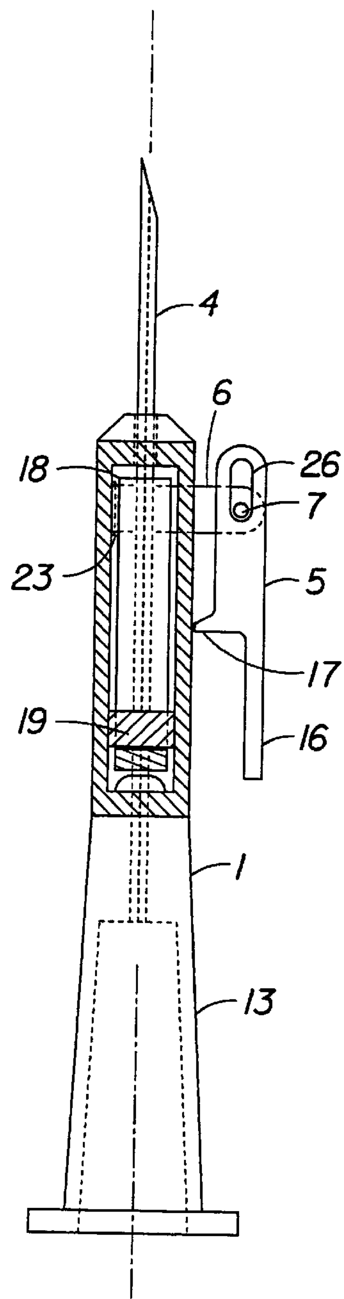
FIG. 7 is a section elevation of the hub chamber and a trigger device.

Referring to FIG. 7 there is shown a section elevation of the hub 13 and the hub chamber 14 as taken through FIG. 3.

The needle cannula 4 is shown with a first end and a second end. The second end of the needle cannula is suitably fixed to the hub 13 and cannot be withdrawn.

The device 1 is shown with trigger means 5 that is comprised of the spring stop 6, the pivot pin 7 the fulcrum 17 the depressors extension 16 the elongated slot 26, the spring stop ridge 23, the hub spring 18 and the spring pin 19.

The spring stop 6 is holding back the hub spring 18 and thereby preventing the hub spring 18 from bending or destroying the needle cannula 4.

Referring to FIG. 8 there is shown a section elevation of the hub 13 and the hub chamber 14 as taken through FIG. 4. Both FIG. 4 and FIG. 8 describes a brief moment after the spring stop 6 has been removed from restraining the hub spring 18 and before the hub spring 18 strikes the needle cannula 4 in hub chamber 14.

The depressor extension 16 has been depressed thereby elevating the pivot pin 7 and rotating the first end of the trigger means about the fulcrum 17. As the pivot pin 7 moves upward 27, it further pulls up on the spring stop 6 wherein the spring stop 6 is withdrawn from the hub chamber 14 thereby releasing the hub spring 18.

Figure 9:
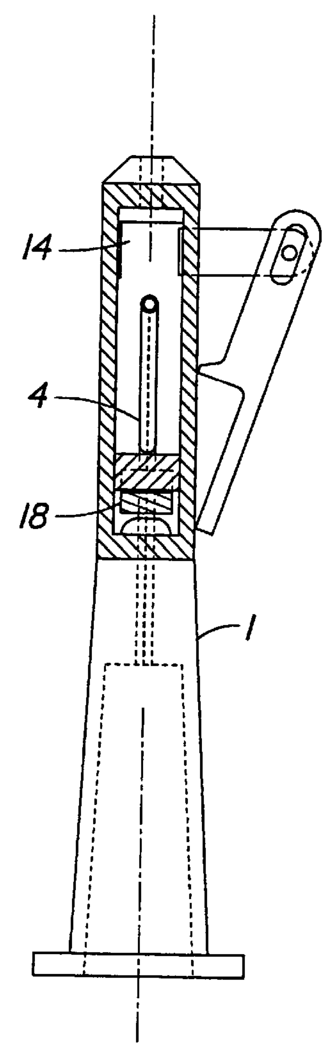
FIG. 9 is a section elevation of the device after the spring stop is pulled.

Referring to FIG. 9 there is shown a section elevation of the device 1 as taken through FIG. 6.

The hub spring 18 has been released and has bent and destroyed the needle cannula 4. The needle cannula 4 has been completely withdrawn into the hub chamber 14 and is destroyed or rendered useless due to its bent up condition; the needle cannula 4 can no longer accidentally prick another person nor can the needle cannula 4 be reused in an illegal manner for drugs or other purposes.

Although the system described in detail supra has been found to be most satisfactory and preferred, many variations are possible. For example the device could be round or square in configuration, the hub could be a slip on connection or the hub could be fixed to the syringe. There could be a number of triggering devices used.

Although the invention has been described with reference to the preferred embodiment, it will be understood by those skilled in the art, that additions, modification, substitutions deletions and other changes not specifically described way be made in the embodiments here in; it should be understood that the details herein are to be interpreted as illustrative and are not in a limiting sense.

What is claimed as invention is:

1. A device wherein a needle cannula is fixed to said device and wherein said device is fixed to a syringe wherein said device is used to inject medication into the body of a patient after said device is used said needle cannula is destroyed, comprising;

a hub wherein said hub has a first end and a second end and wherein said second end of said hub is fixed to said first end of said syringe forming a fluid tight connection with said syringe and wherein said hub has a hollow passage inside to allow for the flow of said medication through said hub;

a hub chamber wherein said hub chamber has a first end, a second end a third end, a fourth end and a hollow inside;

a needle cannula with a first end and a second end and wherein said needle cannula is a hollow tube that will transport said medication from said syringe into the flesh of a body and wherein said second end of said needle cannula is fixed to said first end of said hub;

a hub spring wherein said hub spring has a first end and a second end and said hub spring is partly disposed in said hub chamber and said hub spring is biased;

a trigger means wherein said trigger means is comprised of a depressor bar with a first end and a second end, a fulcrum, a pivot pin and a spring stop wherein said spring stop has a first end and a second end and wherein said second end of said spring stop extends into said inside of said hub chamber and further restrains said based hub spring and wherein said first end of said spring stop is fixed to said pivot pin and wherein said pivot pin fixed to said first end of said depressor bar wherein said second end of said depressor bar is depressed thereby causing said depressor bar to rotate about said fulcrum thereby elevating said first end of said depressor bar and further withdrawing said spring stop from said biased hub spring said hub chamber thereby releasing said biased hub spring and further allowing said biased hub spring to rotate freely about said second end of said biased hub spring wherein said biased hub spring further impacts or strikes said needle cannula thereby bending said needle cannula and further pulling said first end of said needle cannula completely into said hub chamber wherein the pointed first end of said needle cannula is inside of said hub chamber and said needle cannula is completely destroyed in said hub chamber wherein said needle cannula may not be reused or accidentally prick another body.

2. The device of claim 1 wherein a needle cannula guide is formed on said first end of said hub chamber.

3. The device of claim 2 wherein said needle cannula guide guides said needle cannula as said needle cannula is being pulled into said hub chamber and further forces said first end of said needle cannula to remain straight as said needle cannula is being bent and withdrawn into said hub chamber.

4. The device of claim 1 wherein said hub is a threaded lock and wherein said hub may be screwed into said first end of said syringe.

5. The device of claim 1 wherein said hub may be a slip on tip.

6. The device of claim 1 wherein said device may be safely removed from said syringe after said device has been used and said needle cannula has been destroyed.

7. The device of claim 1 wherein said biased hub spring is held in place by a spring pin.

8. The device of claim 1 wherein a spring stop ridge is formed in said hub chamber and said spring stop ridge further supports said spring stop from the thrust of said biased spring.

9. The device of claim 1 wherein said trigger means is activated by the press of a finger or thumb.

10. The device of claim 1 wherein said trigger means is activated by tapping said second end of said depressor bar on a corner of a table of any other hard object.

* * * * *